Feb. 16, 1965 J. R. MITTLEIDER Plant Pat. 2,479
DIANTHUS PLANT
Filed Sept. 23, 1963
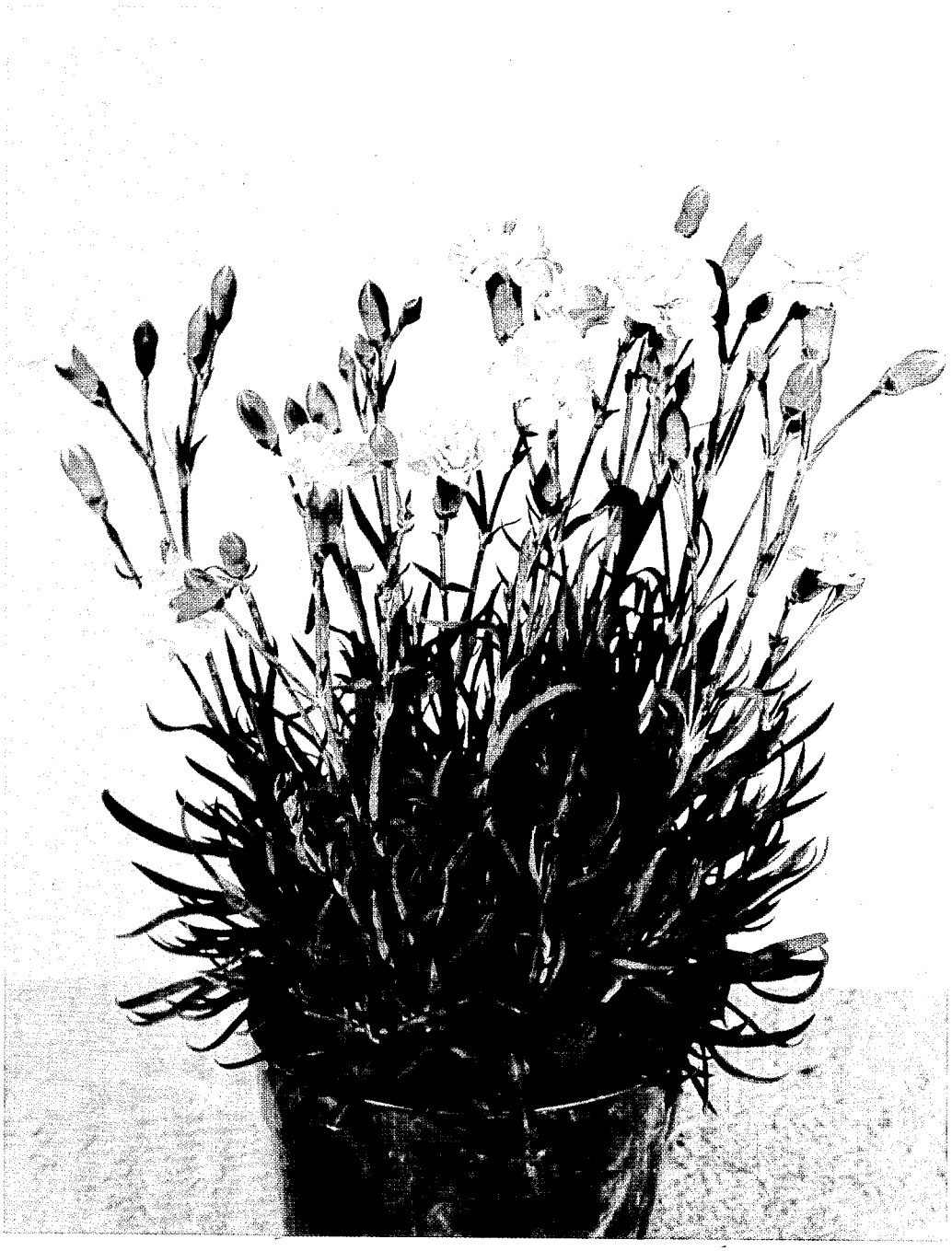
INVENTOR
JACOB R. MITTLEIDER
BY Herbert E. Kidder
AGENT United States Patent Office Plant Pat. 2,479
Patented Feb. 16, 1965

2,479
DIANTHUS PLANT

Jacob R. Mittleider, Loma Linda, Calif., assignor to Milo Academy, Inc., Milo, Oreg., a corporation of Oregon Filed Sept. 23, 1963, Ser. No. 310,963
1 Claim. (Cl. Plt.—71)

The present invention relates to a new and distinct variety of dianthus plant, which is characterized particularly by a low growing, compact, densely tufted plant bearing numerous small, double flowers of a delicate shade of salmon pink with markings of a somewhat darker hue, borne on tall stems up to 10 inches in length, and having a light, spicy, carnation fragrance.

The new and different plant variety is the result of an extensive breeding program at my nursery in Loma Linda, California, seeking new varieties of dianthus that would be especially suitable for mass plantings or edgings, without the necessity of staking the blooms. The characteristics sought were: (1) carnation foliage, (2) ever-blooming habit, (3) compactness, (4) fragrance, (5) full-bodied double blossoms, (6) strong stems, (7) hardiness and disease resistance, (8) pleasing new colors.

The present variety is the result of three separate breeding steps, the first of which was to cross Dianthus Wallace Red (unpatented) with Dianthus Old Spice (Plant Patent No. 499), using the pollen of Old Spice. Wallace Red is a *Dianthus plumarius,* a hybrid of semi-compact habit bearing semi-double red flowers of pleasing hue but no particular fragrance. The flowers are borne on tall, strong stems. Old Spice is a semi-compact plant having *plumarius* characteristics, and bearing coral pink flowers having an outstanding spicy fragrance. However, the flowers are borne on weak stems.

Seedlings from this first cross were selected for foliage, and were pollinated with pollen from Dianthus Ruby Gem (unpatented). Ruby Gem has a dense, compact plant form with short foliage, and bears double, salmon-colored blooms on short stems. The flowers have only a very faint fragrance.

Seedings from this second cross were "selfed"—which is a term for artificially pollinating the plants of a group having the same genes.

Out of some 10,000 seedlings grown from this third pollination, I found one outstanding plant having a low, compact, densely tufted growing habit, with numerous small double flowers of a delicate shade of salmon pink, having markings of a somewhat darker hue. The flowers had a light, spicy, carnation fragrance, and were borne at the ends of tall stems, up to 10 inches in length.

Asexual reproduction of this original plant by cuttings was performed by me in the experimental section of my nursery at Loma Linda, California, and shows that the characteristics and distinctions of the variety come true to form and are established and transmitted through succeeding propagations.

The plant grows best in well-drained, loamy soil, but is not critical as to the pH of the soil. Best blooms are obtained when the plant is grown in full sunlight.

The accompanying drawing shows a typical plant of my new variety, showing the flowers and foliage depicted in color as nearly true as it is reasonably possible to make the same in a color illustration of this character.

The following is a detailed description of my new variety, as based on my observations of specimens grown at Loma Linda, California, with color terminology and identifications in accordance with "A Dictionary of Color" by Maerz and Paul.

Plant:

*Form.*—Compact, growing to a height of two to three inches.

*Growing habit.*—Densely tufted.

*Blooming habit.*—Floriferous, flowering evenly over the entire plant, with blossoms ranging from ¾ of an inch to 1 inch in diameter, and ranging in number from 3 or 4 on one year old plants grown in three-inch pots, up to 20 or 30 on two year old plants.

*Blooming season.*—Perpetual in southern California, or wherever the mean temperature is above 50° F. Where the mean temperature drops below 50° F., the plant becomes dormant and ceases to bloom. Maximum bloom in southern California occurs from March through July, and in October and November; while minimum bloom occurs from August to October and from December through February.

*Foliage size.*—Maximum size of mature leaves on thrifty young plants is approximately 2 to 3 inches in length, by three-sixteenths of an inch in width.

*Quantity.*—Abundant.

*Shape.*—Lanceolate, or grass-like.

*Color.*—Growing under good conditions, the color of mature leaves is a deep true green, corresponding almost exactly to Aspen Green (Plate 31–C–6 in Maerz and Paul's Color Dictionary).

*Texture.*—Glaucous.

Flower:

*Size.*—The maximum size is about ¾ of an inch to 1 inch in diameter, by ⅜ to ½ inch high.

*Borne.*—At the end of the stems.

*Stem.*—Stiff and upright, approximately 8 to 10 inches in length.

*Petalage.*—Double.

*Color.*—The flower is a delicate salmon pink (Plate 1–G–8, Maerz and Paul) with irregular markings of a slightly darker hue (Plate 1–J–8, Maerz and Paul).

*Petals.*—Of obovate form with regularly crenate margins. The size of the individual petals is about ½ inch to ¾ inch in length, by about ⅜ inch in width.

*Fragrance.*—Light, spicy, carnation-like.

*Calyx.*—Spreading at the tip, with acuminate teeth, and approximately ¾ inch in length.

Compared to other well-known dianthus plants, this new variety is distinguished by its low-growing, compact form, with small, delicate salmon pink flowers carried at the ends of rather long, stiffly upright stems, said flowers having slightly darker markings, and having a light, spicy, carnation-like fragrance.

I claim:

A new and distinct variety of dianthus plant, substantially as shown and described herein, characterized particularly by its floriferous blooming habit, low-growing, compact, densely tufted plant form, usually not exceeding three inches in height, and bearing many small, double flowers of a delicate salmon pink with markings of slightly darker hue, said flowers having a light, spicy, carnation-like fragrance, and being borne on the ends of stiff, upright stems approximately 8 to 10 inches in height.

No references cited.